United States Patent
Pilkington et al.

(10) Patent No.: US 10,354,211 B1
(45) Date of Patent: Jul. 16, 2019

(54) ACCOUNT PRIORITIZATION FOR PATIENT ACCESS WORKFLOW

(71) Applicant: Passport Health Communications, Inc., Franklin, TN (US)

(72) Inventors: Edmond Chase Pilkington, Rockvale, TN (US); Joseph M. Magee, Drexel Hill, PA (US); Howard Bright, Kingston Springs, TN (US); Michael Cohn Moreau, Nashville, TN (US); Lance Clifford Mansfield, Seattle, WA (US)

(73) Assignee: PASSPORT HEALTH COMMUNICATIONS INC., Franklin, TN (US)

( * ) Notice: Subject to any disclaimer, the term of this patent is extended or adjusted under 35 U.S.C. 154(b) by 0 days.

(21) Appl. No.: 13/770,660

(22) Filed: Feb. 19, 2013

Related U.S. Application Data

(60) Provisional application No. 61/600,600, filed on Feb. 18, 2012, provisional application No. 61/765,317, filed on Feb. 15, 2013.

(51) Int. Cl.
*G06Q 50/22* (2018.01)
*G06Q 10/06* (2012.01)

(52) U.S. Cl.
CPC ......... *G06Q 10/0633* (2013.01); *G06Q 50/22* (2013.01)

(58) Field of Classification Search
None
See application file for complete search history.

(56) References Cited

U.S. PATENT DOCUMENTS

| | | | | |
|---|---|---|---|---|
| 7,606,721 | B1* | 10/2009 | Donnelly et al. | 705/2 |
| 8,688,480 | B1* | 4/2014 | Singh et al. | 705/4 |
| 2002/0026328 | A1* | 2/2002 | Westerkamp | G06F 19/322 |
| | | | | 705/2 |
| 2003/0140044 | A1 | 7/2003 | Mok et al. | |
| 2004/0230458 | A1 | 11/2004 | Takayama et al. | |
| 2004/0244005 | A1* | 12/2004 | Ancier | G06Q 10/109 |
| | | | | 718/103 |

(Continued)

OTHER PUBLICATIONS

Edmond Chase Pilkington et al., U.S. Appl. No. 13/770,587, Exception-Based Integrated Patient Access Workflow, filed Feb. 19, 2013.

(Continued)

*Primary Examiner* — Hiep V Nguyen
(74) *Attorney, Agent, or Firm* — Merchant & Gould

(57) ABSTRACT

Account prioritization for a patient access workflow is provided. The patient access workflow may be an exception-based integrated workflow. An indication of discrepant data, missing data, or input/user-interaction that may be needed for performance of a patient access workflow process for a patient account may be provided via alerts displayed in an integrated user interface. A prioritization engine may determine a priority score for a patient account based on various determining factors and weightings applied to each determining factor. The patient account may be placed in a queue of accounts needing to be cleared in order by priority score, such that when a user selects to receive a next account to clear, the account with the highest priority score may be provided to the user. Accordingly, a user may be able to address and resolve alerts to ensure patient access workflow processes are performed prior to a healthcare encounter.

17 Claims, 6 Drawing Sheets

(56) References Cited

U.S. PATENT DOCUMENTS

| | | |
|---|---|---|
| 2005/0273363 A1 | 12/2005 | Lipscher et al. |
| 2006/0129435 A1 | 6/2006 | Smitherman et al. |
| 2007/0022086 A1 | 1/2007 | Elsholz |
| 2007/0027714 A1 | 2/2007 | Fenno |
| 2008/0027965 A1* | 1/2008 | Garrett et al. .............. 707/102 |
| 2009/0216562 A1 | 8/2009 | Faulkner et al. |
| 2011/0029330 A1* | 2/2011 | Paddock, III ......... G06Q 40/08 705/4 |
| 2013/0046558 A1 | 2/2013 | Landi et al. |
| 2013/0046560 A1 | 2/2013 | Theus et al. |

OTHER PUBLICATIONS

Office Action dated Nov. 7, 2014, in co-pending U.S. Appl. No. 13/770,587, 12 pgs.
Office Action dated Apr. 6, 2015, in co-pending U.S. Appl. No. 13/770,587, 12 pgs.
Office Action dated Oct. 28, 2015, in co-pending U.S. Appl. No. 13/770,587, 17 pgs.
Office Action dated May 31, 2016, in co-pending U.S. Appl. No. 13/770,587, 15 pgs.
Office Action dated Dec. 13, 2017, in co-pending U.S. Appl. No. 13/770,587, 9 pgs.
Office Action dated Nov. 28, 2016, in co-pending U.S. Appl. No. 13/770,587, 8 pgs.
Office Action dated May 18, 2018, in co-pending U.S. Appl. No. 13/770,587, 11 pgs.
Office Action dated Nov. 8, 2018, in co-pending U.S. Appl. No. 13/770,587, 14 pgs.
Notice of Allowance dated Apr. 24, 2019, in co-pending U.S. Appl. No. 13/770,587, 8 pgs.

* cited by examiner

ACCOUNT PRIORITIZATION FOR PATIENT ACCESS WORKFLOW

CROSS-REFERENCE TO RELATED APPLICATIONS

The present application claims priority to U.S. Provisional Patent Application No. 61/600,600 titled "Exception-Based Alert and Prioritization System" filed Feb. 18, 2012, and U.S. Provisional Patent Application No. 61/765,317 titled "Financial Triage" filed Feb. 15, 2013, and is related to U.S. patent application Ser. No. 13/770,587 titled "Exception-Based Integrated Patient Access Workflow" filed Feb. 19, 2013, the disclosures of which are incorporated herein by reference in their entireties.

BACKGROUND

When a patient seeks healthcare services from a healthcare provider, various processes may be performed between the time when patient data is received and when healthcare services are provided. The various processes may make up a patient access workflow and may include such processes as, but are not limited to, verifying coverages (e.g., insurance eligibility and verification), verifying demographic data to help ensure that a patient's demographic data is correct for insurance claims, billing statements, etc., checking payer compliance to help screen for payer medical necessity and precertification and to aid with accuracy in orders, coding and billing, estimating a payment amount, determining a patient's financial situation to help mitigate the risk of late payments and possible need for collections later on, and collecting payment for services.

One or more users, such as administrative users, may utilize one or more tools for patient account clearance (performing the patient access workflow). A user may be provided with a plurality of patient accounts needing to be cleared prior to the patients arriving for a healthcare encounter. The user may clear accounts in an order in which the accounts are provided to him, or may analyze various accounts to determine which one may be deemed a higher priority to clear next. As can be appreciated, a first-in-first-out approach may oftentimes not be effective. For example, if an account is received that may take longer to process because of various factors, but has a short lead time before the patient arrives for a healthcare encounter, the patient access workflow process may not be completed prior to when the patient arrives for healthcare services. Additionally, relying on a user to determine which account may be a higher priority account to clear next may be unreliable and inaccurate.

It is with respect to these and other considerations that the present invention has been made.

SUMMARY

Embodiments of the present invention provide account prioritization for a patient access workflow. The patient access workflow may be an exception-based integrated workflow, wherein an indication of discrepant data, missing data, or input/user-interaction that may be needed for performance of a patient access workflow process for a patient account may be provided via alerts displayed in an integrated user interface. Embodiments may include a prioritization engine operable to determine a priority score for a patient account based on various determining factors and weightings applied to each determining factor. The patient account may be placed in a queue of accounts needing to be cleared in order by priority score, such that when a user selects to receive a next account to clear, the account with the highest priority score may be provided to the user. Accordingly, a user may be able to address and resolve alerts to ensure patient access workflow processes are performed prior to a healthcare encounter.

DETAILED DESCRIPTION

Figure 1:
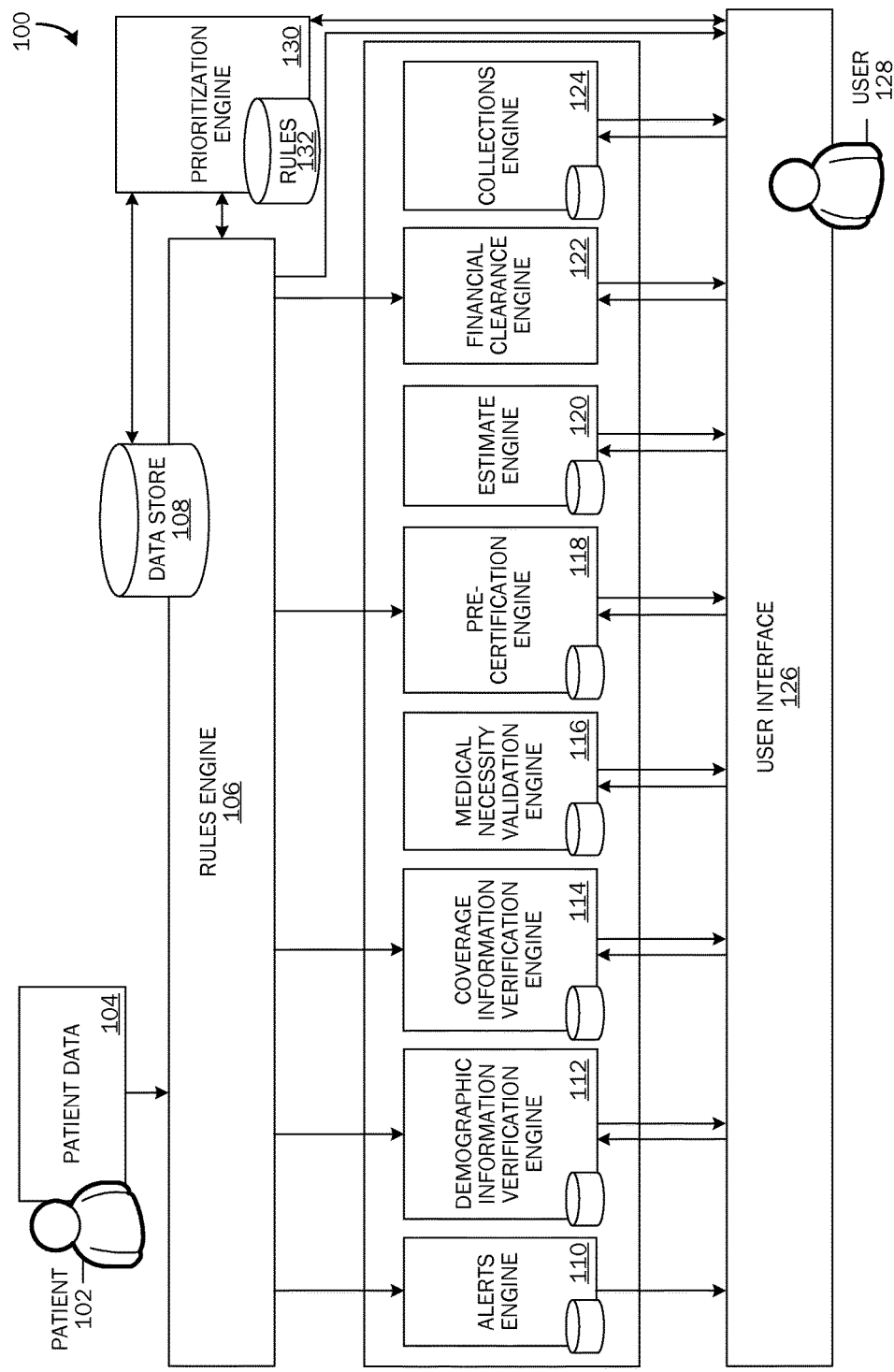
FIG. 1 is a simplified block diagram of a high-level system architecture with which embodiments of the invention may be implemented.

As briefly described above, embodiments of the present invention provide account prioritization for patient account clearance. A patient access workflow may help healthcare providers to verify patient information on the front-end, which may lead to a reduction in errors, and clean up on the back-end for ensuring payment certainty. Patient accounts may be cleared via the patient access workflow prior to the patient receiving healthcare services. Discrepant data, missing data, or input/user-interaction that may be needed for completing an account clearance process of a patient account may be determined and communicated to a user via alerts displayed on a user interface. Users may be provided with a plurality of accounts comprising various alerts that may need to be resolved in order to complete the account clearance process. Depending on the alerts, historical data, and various factors (e.g., immediacy, amount of work, type of coverage, demographic data, etc.), a priority score may be determined for each account. Accounts may be placed in a queue based on their priority scores, such that when a user selects to receive a next account to clear, the account with the highest priority score may be provided to the user. Accordingly, patient accounts may be cleared in an order that may be optimal for the healthcare provider, for example, to mitigate risk of not receiving payment for a patient healthcare encounter.

These embodiments may be combined, other embodiments may be utilized, and structural changes may be made without departing from the spirit or scope of the present invention. The following detailed description is therefore not to be taken in a limiting sense, and the scope of the present invention is defined by the appended claims and their equivalents. Referring now to the drawings, in which like numerals refer to like elements throughout the several figures, embodiments of the present invention and an exemplary operating environment will be described.

Referring now to FIG. 1, a simplified block diagram of a high-level system architecture 100 with which embodiments of the invention may be implemented is shown. Patient data 104 may be inputted into an information system, for example, a healthcare provider information system. Patient data 104 may include one or more of demographics data, admissions data, pre-registration data, coverage data, and scheduling data. If a guarantor of the patient's account is different than the patient 102, patient data 104 may also include data associated with the guarantor. According to embodiments, demographic data may include details of a patient 102 such as, but not limited to, the patient's name, address, phone number(s), social security number, date of birth, gender, marital status, emergency contact information, employment status and details, student status and details, insurance information, guarantor information, etc.

When patient data 104 is received, a rules engine 106 may be triggered to apply various rules and intelligence for verifying the received patient data 104 against data in one or more data sources 108. According to embodiments, according to various rules, requests may be sent automatically to one or more patient access workflow engines 112, 114, 118, 122 to perform one or more patient access workflow processes. According to one embodiment, a rule may be applied to automatically send a request to a demographic information verification engine 112 to cross-match a name, address, etc. of a patient 102 or the guarantor of the patient's account (demographic information included in received patient data 104) with information stored in one or more data sources 108. According to another embodiment, a rule may be applied to automatically send a request to a coverage information verification engine 114 to verify insurance coverages a patient 102 (or guarantor) claims to have. According to another embodiment, a rule may be applied to automatically send a request to a pre-certification engine 118 to identify procedures that may require pre-certification according to a patient's 102 coverage plan. According to another embodiment, a rule may be applied to automatically send a request to a financial clearance engine 122 to collect credit and financial information of a patient 102 (or guarantor of the patient's account) to determine the patient's (or the patient's guarantor's) financial situation. The requests may be sent by the rules engine 106 automatically to one or more patient access workflow engines. That is, a user 128 may not be required to manually send a request to perform a patient access workflow process.

The data sources 108 may store data and metadata such as patient encounter data, patient coverage data, alerts, results from one or more patient access workflow processes, and collections amounts. Stored data and metadata, discrepant or missing patient data 104 may be automatically corrected and/or one or more alerts may be provided. Embodiments may comprise an alerts engine 110 operable to provide alerts to notify a user 128 (e.g., administrative user, patient 102, etc.) of potential problems (e.g., missing information, erroneous information, etc.) or additional steps needed to be completed for performing one or more processes of a patient access workflow. Providing alerts of potential problems or additional steps may provide for an exception-based workflow where a user 128 may be able to pre-authorize accounts with potential problems or accounts needing the attention of a user 128. Results from one or more patient access workflow engines 112, 114, 116, 118, 120, 122, 124 and alerts notifying a user of potential problems or additional actions may be presented via a user interface 126.

With reference again to FIG. 1, the system 100 may comprise a demographic information verification engine 112 operable to verify demographic data to help ensure that a patient's demographic data is correct for insurance claims, billing statements, etc. A request may be sent to a demographic information verification engine 112 either automatically from the rules engine 106 or from a user 128 to cross-match a name, address, etc. of the patient 102 or the guarantor of the patient's account (demographic information included in received patient data 104) with information provided by one or more third party data sources (e.g., utility billing records, phone company listings, credit bureaus, the United States Social Security Administration's death master file, United States Postal Service® change of address records, state drivers license databases, magazine subscription records, moving company records, mobile phone application information, rental agreements, rental applications, etc.). Incorrect demographic information such as spelling discrepancies, incorrect address information, an incorrect social security number, an incorrect date-of-birth, etc. may be discovered and an alert 208 may be provided. Results from the demographic information verification engine 112 and any alerts may be displayed on the user interface 126. For more information about one embodiment of a demographic information verification engine 112, please see U.S. patent application Ser. No. 13/651,051 titled "Information Standardization and Verification" filed on Oct. 12, 2012.

The system 100 may also include a coverage information verification engine 114. A request may be sent to the coverage information verification engine 114 either automatically from the rules engine 106 or from a user 128 to perform a coverage (i.e., insurance) eligibility verification process. According to an embodiment, the coverage information verification engine 114 may be operable to perform a query for coverages for a patient 102 (or guarantor).

The system 100 may also include a medical necessity validation engine 116. A request may be sent to the medical necessity validation engine 116 through the user interface 126 to perform a check of a patient order against payer rules for medical necessity, frequency, duplication, modifiers, etc. to help produce a clean claim billed with less chance of denial. For example, medical necessity validation may identify potentially denied claims prior to submission, allowing corrections to take place, eliminating rebilling costs, and increasing staff self-corrections. Based on Medicare and commercial payer rules (e.g., inpatient hospitalization for a treatment that could be safely and adequately provided on an outpatient bases, cosmetic surgery, treatment provided for the convenience of a patient 102, etc.), issues that may result in a denied claim may be detected, and results from the medical necessity validation engine 116 may be displayed on the user interface 126.

According to embodiments, the system 100 may also include a pre-certification engine 118. A request may be sent to the pre-certification engine 118 either automatically from the rules engine 106 or from a user 128 through the user interface 126 to identify procedures that may require pre-certification. Results from the pre-certification engine 118 may be displayed on the user interface 126.

The system may comprise an estimate engine 120, which may be operable to determine an estimate of an amount a patient 102 (or guarantor) may be expected to pay for healthcare services. A request for an estimate may be sent via the user interface 126. The estimate engine 120 may determine an estimate of a patient's responsibility based on average charges and benefit information such as deductible amounts, co-pay amounts, co-insurance amounts, etc.

According to embodiments, a financial clearance engine 122 may be included in the system 100. A request may be sent automatically by the rules engine 106 or by a user 128 via the user interface 126 to the financial clearance engine 122 to communicate with one or more third party data sources to collect credit and financial information of a patient 102 (or guarantor of the patient's account). Collected credit and financial information of a patient 102 (or guarantor of the patient's account) may be utilized to assess a patient's (or guarantor's) financial situation for determining a probability of receiving payment for healthcare services rendered.

The system 100 may also include a collections engine 124. The collections engine 124 may be operable to help patients know what they owe and how the balance will be paid. For example, embodiments may provide an explanation to patients about what the patient 102 (or guarantor) will owe at the time of service, may provide an estimate of current services and balances from previous visits, may determine a patient's eligibility for Medicaid and charity before asking for payment, may provide for enrolling eligible patients for Medicaid before rendering service and may extend hospital charity to those who qualify, may securely accept payment upfront for smaller balances, and may extend payment terms and fundraising options for larger balances.

According to embodiments, the system 100 may include a prioritization engine 130. The prioritization engine 130 may be operable to receive patient data 104 and information determined by one or more of the patient access workflow engines 112, 114, 116, 118, 120, 122, 124 to prioritize a next account to be cleared. Accounts may be prioritized according to a priority score calculated according to weightings assigned to various determining factors. The information determined by the one or more patient access workflow engines may be provided directly to the prioritization engine 130, or alternatively, may be stored in a data store 108 and accessed by the prioritization engine 130.

There may be various determining factors utilized to calculate a priority score to prioritize an account, and may be customizable via rules 132 used by the prioritization engine 130. Determining factors may include, but are not limited to, amount of time until a scheduled healthcare encounter (e.g., urgency), an estimated amount of time to process a patient's account through the patient access workflow (e.g., including a number/type of alerts 208 a user 128 may need to clear to process the patient's account), cost of a service or a procedure to be provided or performed, whether a patient is a self-pay patient vs. a patient with insurance coverage, the network/type of insurance coverage a patient has (e.g., HMO vs. PPO vs. Medicare), which payer is providing insurance coverage, the specific service or procedure the patient is receiving, etc. Different weightings may be given to each of the various factors for determining an order of patient accounts to process.

As an example, consider that a first patient 102 and a second patient 102 may be scheduled for healthcare encounters, for example, the first patient 102 may be scheduled for a hip replacement surgery and the second patient 102 may be scheduled for treatment for a broken finger. Both patients' account may be processed through the patient access workflow prior to the appointments for the healthcare services to be performed. Additionally, if any issues have been detected, any alerts 208 that have been provided may need to be resolved prior to the patients 102 receiving their healthcare services. The prioritization engine 130 may be utilized to determine an order of patient accounts to process. In this example case, a higher weight for the cost factor may be given to the first patient's account over the second patient's 102 account, because of the cost associated with the first patient procedure is greater than the cost of the procedure to be performed for the second patient 102.

In another example case, a higher weight for a coverage factor may be given to a self-pay patient's account over an account of a patient 102 who has healthcare insurance. As can be appreciated, a healthcare provider may want to ensure they have correct demographic data for the self-pay patient, for example, to increase the probability of the patient 102 receiving his invoice. Financial aid may also be extended to the self-pay patient 102, which may need to be established prior to when the self-pay patient receives healthcare services.

As another example, a higher weight for the coverage factor may be given to an account of a patient 102 who has commercial insurance coverage over a Medicare patient's account. For example, completing the patient access workflow process prior to the appointment of the patient 102 who has commercial insurance coverage may increase the probability of an approved claim (and help to ensure payment for services performed), whereas the likelihood of receiving payment from Medicare may be greater.

As another example, a higher weight for the coverage factor may be given to an account of a patient 102 with an HMO (Health Maintenance Organization) plan over a an account of a patient 102 with a PPO (Preferred Provider Organization) plan because there may be more patient access workflow processes to perform (e.g., referrals, pre-certifications, etc.) to clear an account with HMO coverage.

If a patient's account has been flagged with several alerts 208 to be resolved for the patient access workflow process to be completed, a higher weight for a time factor may be given to the patient's account over another patient's account with fewer alerts 208 to be resolved. What is required to resolve an alert 208 may also be factored into determining a priority of an account. For example, an account may have more alerts 208 than another account, but the types of issues associated with the alerts may be less time-consuming to resolve than the few issues associated with the other account.

Determining factors and rules 132 may be based on historical data. For example, a particular payer may have a history of denying claims for a particular procedure, such as a knee replacement, while another payer typically does not dispute claims for the same procedure. Accordingly, if a patient is scheduled for a knee replacement and has coverage with the payer with a history of denying claims for knee replacements, a higher weighting for a factor may be given to the patient's account because of possible issues the healthcare provider may have with receiving approval from the payer for the procedure.

As another example, historical data may provide statistical information showing that patients 102 with a certain zip code may have a higher propensity for not paying. Accordingly, a higher weighting for a demographic factor may be given to a patient's account with a certain zip code.

Figure 2:
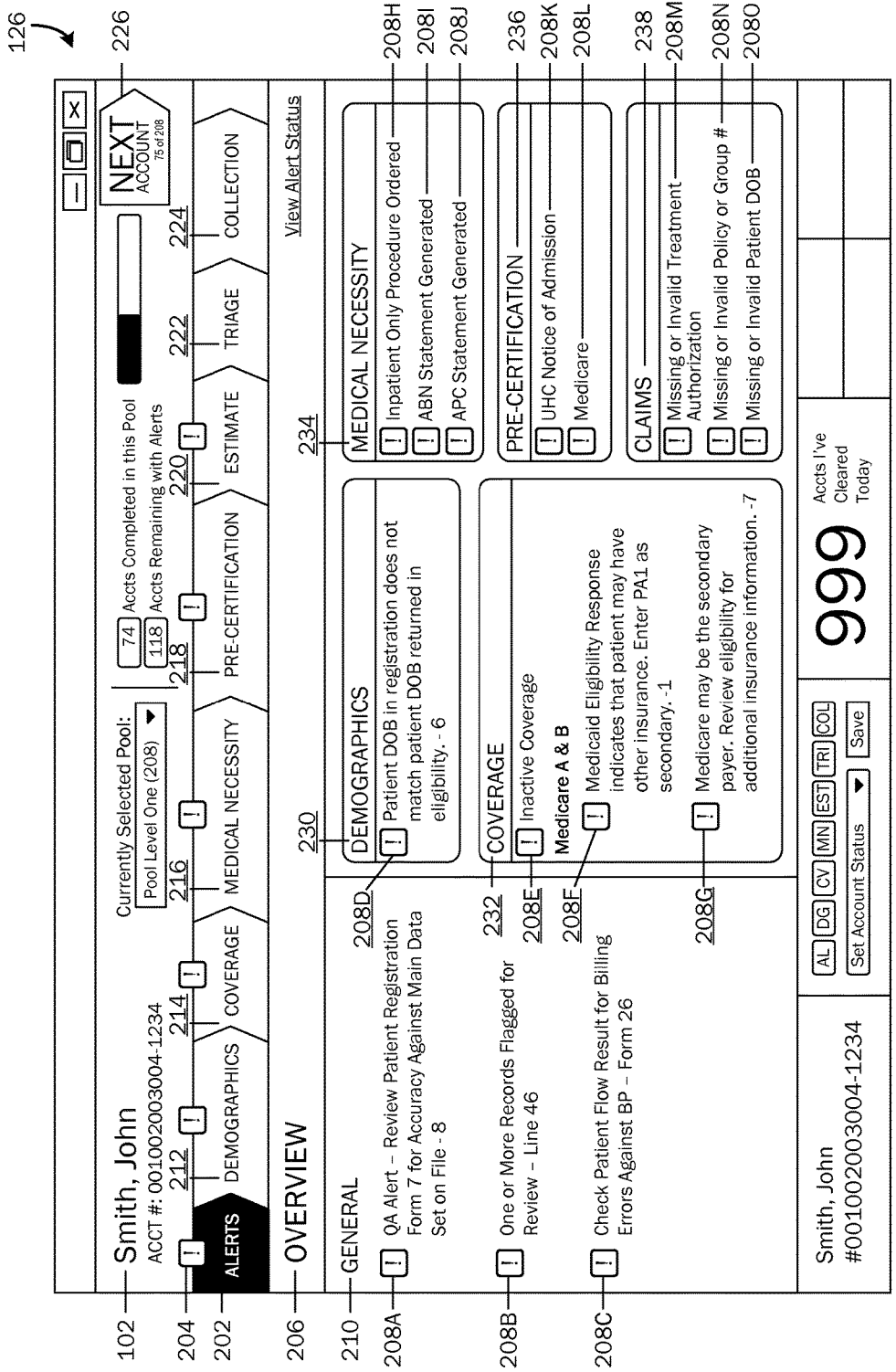
FIG. 2 is an illustration of an example overview page displaying alerts and a "next" button.

Having described a high-level system architecture 100 with which embodiments of the invention may be implemented, FIG. 2 illustrates the user interface 126 displaying an overview page 206 of alerts 208 for various patient access workflow processes. As illustrated, the user interface 126 may include a patient's 102 name and account number. Selectable user interface controls 202, 212, 214, 216, 218, 220, 222, 224 may be provided for accessing a user interface page for each of the various patient access workflow processes. For example, selection of an "alerts" user interface (UI) control 202 may provide a display of the overview page 206 as illustrated. Selection of a "demographics" UI control 212 may provide a display of a demographics page. A graphical element, such as an exclamation point icon (herein referred to as an alert icon 204), may be displayed on or near selectable UI controls 202, 212, 214, 216, 218, 220, 222, 224 associated with a patient access workflow process that has an identified issue or alert 208. As illustrated, an alert icon 204 is displayed above the "alerts" UI control 202, the "demographics" UI control 212, a "coverage" UI control 214, a "medical necessity" UI control 216, a "pre-certification" UI control 218, and an "estimate" UI control 220, indicating that one or more alerts 208 have been identified for the demographics, coverage, medical necessity, pre-certification, and estimate processes.

The overview page 206 may provide a display of alerts 208 sorted by category or by patient access workflow process. For example, alerts 208 may be in a general alerts category 210, a demographics alerts category 230, a coverage alerts category 232, a medical necessity alerts category 234, a pre-certification alerts category 236, and a claims alerts category 238.

An alert icon 204 may be displayed with each alert 208. Alert icons 204 may be selectable, wherein selection of an alert icon 204 may provide a display of further information associated with the alert 208 or may provide a display of a UI page of the associated patient access workflow process engine 110, 112, 114, 116, 118, 120, 122, 124. A user 128 may be able to add or edit data, complete a task, etc. to address alerts via UI pages of patient access workflow processes.

A "next" control 226 may be provided, which when selected, may provide a next account for a user 128 to work on next (an account for which to clear alerts 208). According to embodiments, the next account for a user 128 to work on next may be determined by the prioritization engine 130.

Figure 3:
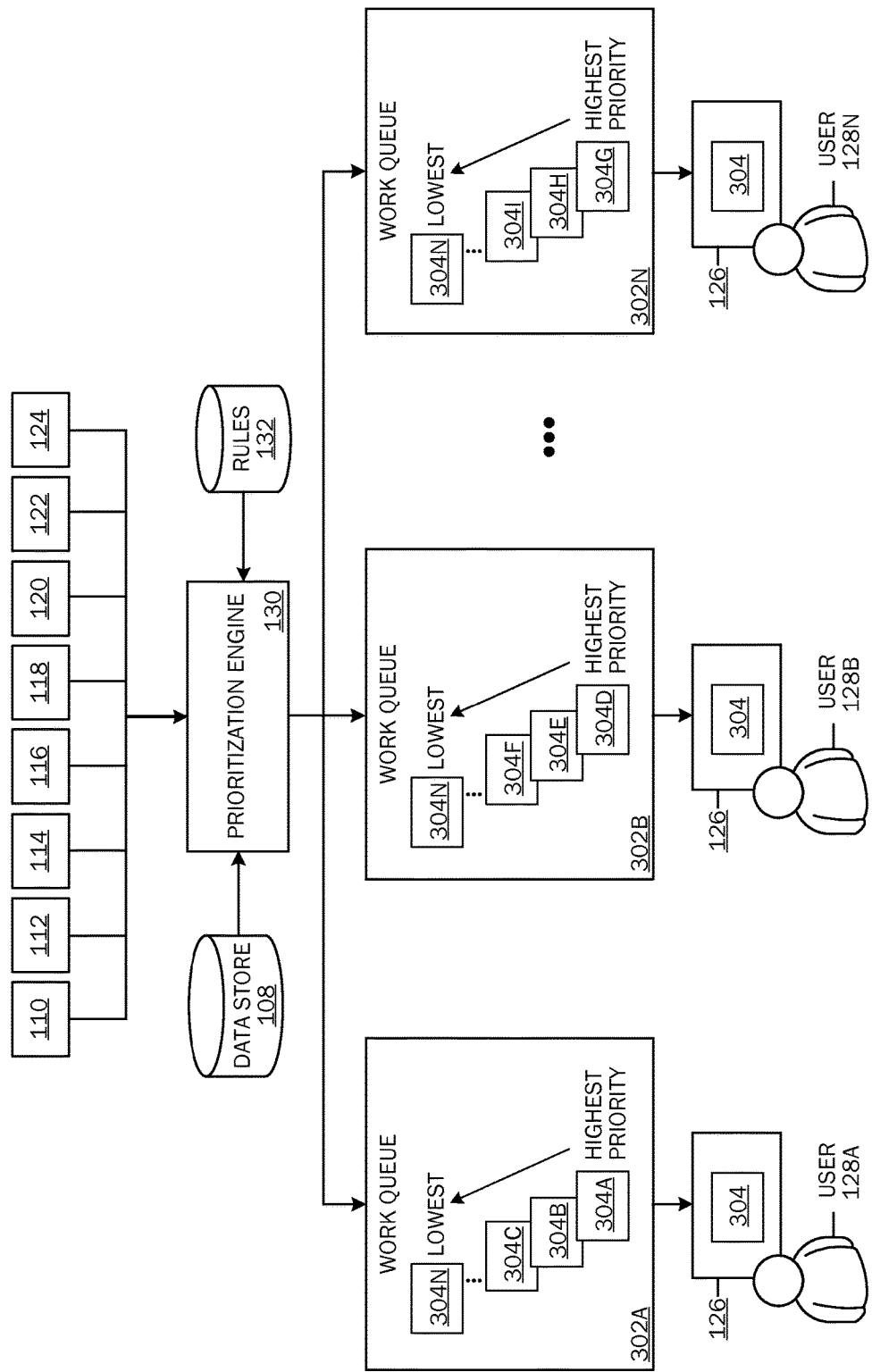
FIG. 3 is an illustration of a prioritization system according to one embodiment.

Referring now to FIG. 3, one embodiment of automatically providing a work queue based on account prioritization for users 128 according to one embodiment. As illustrated in FIG. 3, results from one or more patient access workflow engines 110, 112, 114, 116, 118, 118, 120, 122, 124, data stored in the data store 108 may be provided to the prioritization engine 130. Rules 132 may be applied, and accounts may be prioritized according to weightings of various factors. In the scenario illustrated in FIG. 3, a group of users 128, whose job includes clearing patient accounts 304, may utilize the user interface 126 described above to clear patient accounts 304 using one or more of the patient access workflow processes. Each user 128 may be provided with a queue 302 of patient accounts 304 to clear. The patient accounts 304 may be provided in an order in each queue 302 such that an account 304 with a higher priority weighting may be provided first and then in descending priority weighting order. For example and as illustrated in FIG. 3, patient accounts 304A, 304D, and 304G may be the highest priority patient accounts, followed by 3046, 304E, and 304H, and so on.

Figure 4:
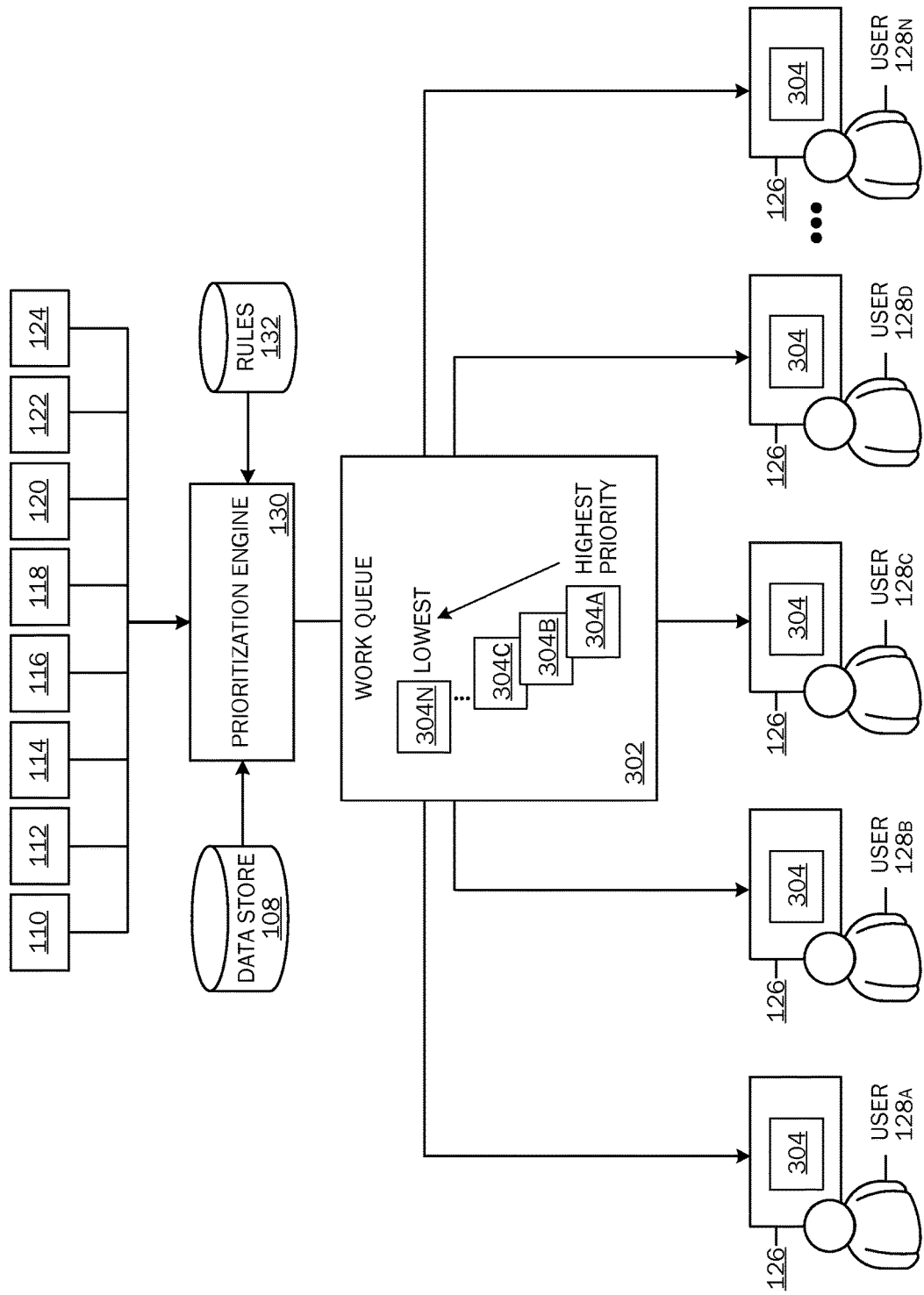
FIG. 4 is an illustration of a prioritization system according to another embodiment.

According to another embodiment and as illustrated in FIG. 4, one queue 302 of patient accounts 304 to clear may be provided for a plurality of users 128. The patient accounts 304 may be prioritized by the prioritization engine 130 as described above. As a user 128 requests a patient account 304 to process, the next account 304 in the queue 302 may be provided to the user 128 via the user interface 126.

Figure 5:
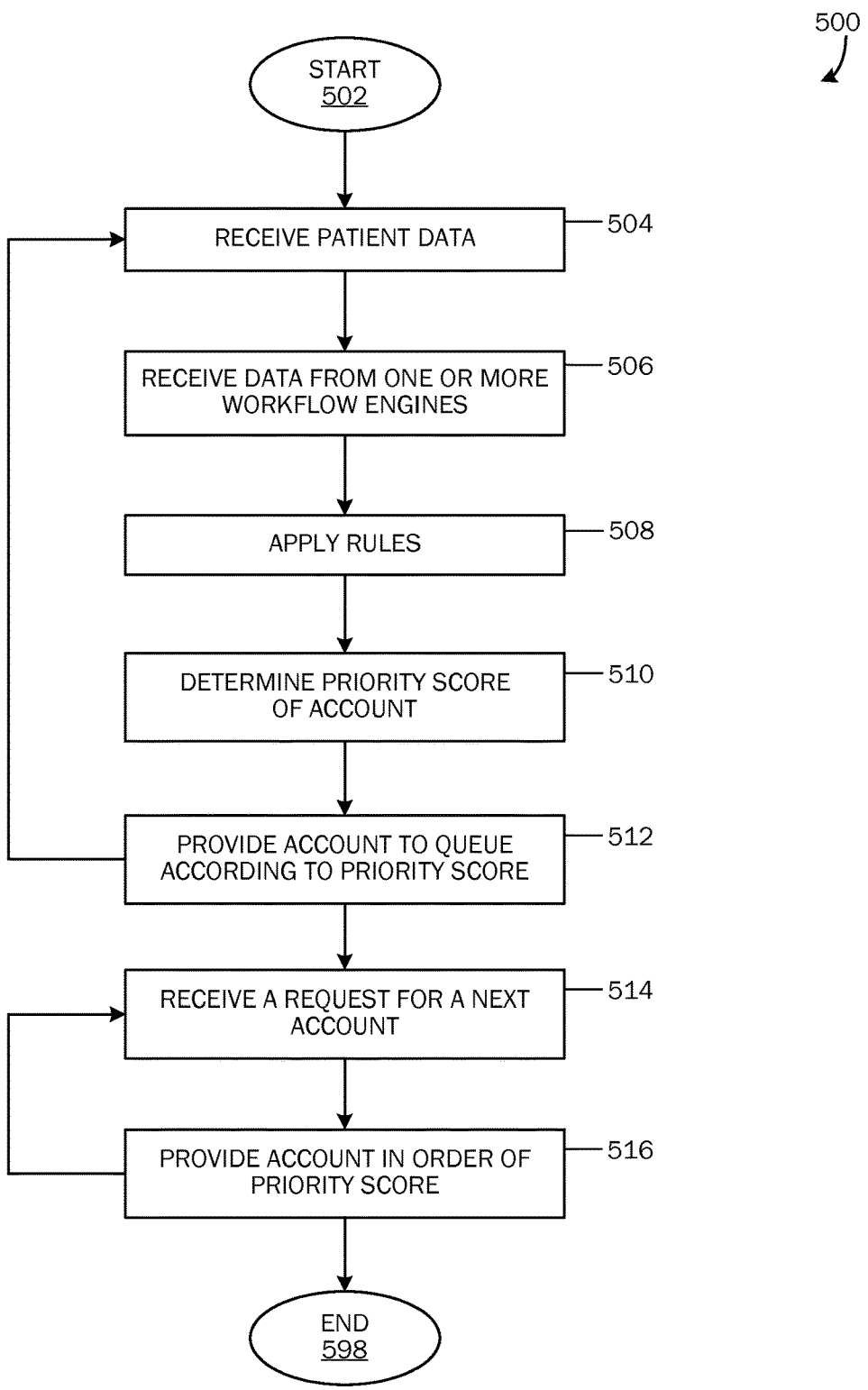
FIG. 5 is a flow chart of a method of providing account prioritization for patient access workflow according to an embodiment.

FIG. 5 illustrates a flow chart of a method 500 of providing account prioritization according to an embodiment. The method 500 starts at OPERATION 502 and proceeds to OPERATION 504, where patient data 104 associated with a patient account 304 may be received. As described above, patient data 104 may include one or more of demographics data, admissions data, pre-registration data, coverage data, and scheduling data and may be entered into an information system, for example, a healthcare provider information system.

When patient data 104 is received, the method 400 may proceed to OPERATION 506, where data from one or more patient access workflow engines 110, 112, 114, 116, 118, 120, 122, 124 may be received. That is, results from one or more of demographics information verification, coverage information verification, medical necessity validation, pre-certification, estimation, financial clearance, or collections may be received by the prioritization engine 130. The results may include alerts 208 determined by the one or more patient access workflow engines for which a user 128 may need to resolve to clear a patient's account 304.

At OPERATION 508, various rules 132 may be applied, wherein the rules 132 may provide weightings for various determining factors. As described above, determining factors may include, but are not limited to, amount of time until a scheduled healthcare encounter, an estimated amount of time to process a patient's account 304 through the patient access workflow (e.g., including a number/type of alerts 208 a user 128 may need to clear to process the patient's account 304), cost of a service or a procedure to be provided or performed, whether a patient is a self-pay patient vs. a patient with insurance coverage, the network/type of insurance coverage a patient has (e.g., HMO vs. PPO vs. Medicare), which payer is providing insurance coverage, the specific service or procedure the patient is receiving, etc.

At OPERATION 510, a priority score for an account 304 may be determined. The priority score may be calculated based on determining factors associated with the account 304 and with the weightings applied to the factors. The method 500 may proceed to OPERATION 512, where an account 304 may be placed in a queue 302 and arranged in an order according to priority score where the account 304 with a highest priority score may be the first account out when a request is made for a next account 304. OPERATIONS 504-512 may repeat for each patient account 304 received.

At OPERATION 514, a request for a next account 304 may be received. For example, a user 128 may select a "next" control 226 via a user interface 126 to receive a next account 304 for which to clear alerts 208 to complete a account clearance process. At OPERATION 516, a next account 304 may be provided to the user 128 via the user interface 126, wherein the next account 304 may be the highest priority level account 304 currently in the queue 302. Accordingly, the user 128 may utilize one or more patient access workflow processes to complete the account clearance process for the patient account 304. OPERATIONS 514-516 may repeat each time a user 128 clear an account 304 and needs a next account 304 to clear. The method 500 may end at OPERATION 598.

Embodiments of the invention may be implemented via local and remote computing and data storage systems. Such memory storage and processing units may be implemented in a computing device, such as computing device 600 of FIG. 6. Any suitable combination of hardware, software, or firmware may be used to implement the memory storage and processing unit. For example, the memory storage and processing unit may be implemented with computing device 600 or any other computing devices 618, in combination with computing device 600, wherein functionality may be brought together over a network in a distributed computing environment, for example, an intranet or the Internet, to perform the functions as described herein. Such systems, devices, and processors (as described herein) are examples and other systems, devices, and processors may comprise the aforementioned memory storage and processing unit, consistent with embodiments of the invention.

Figure 6:
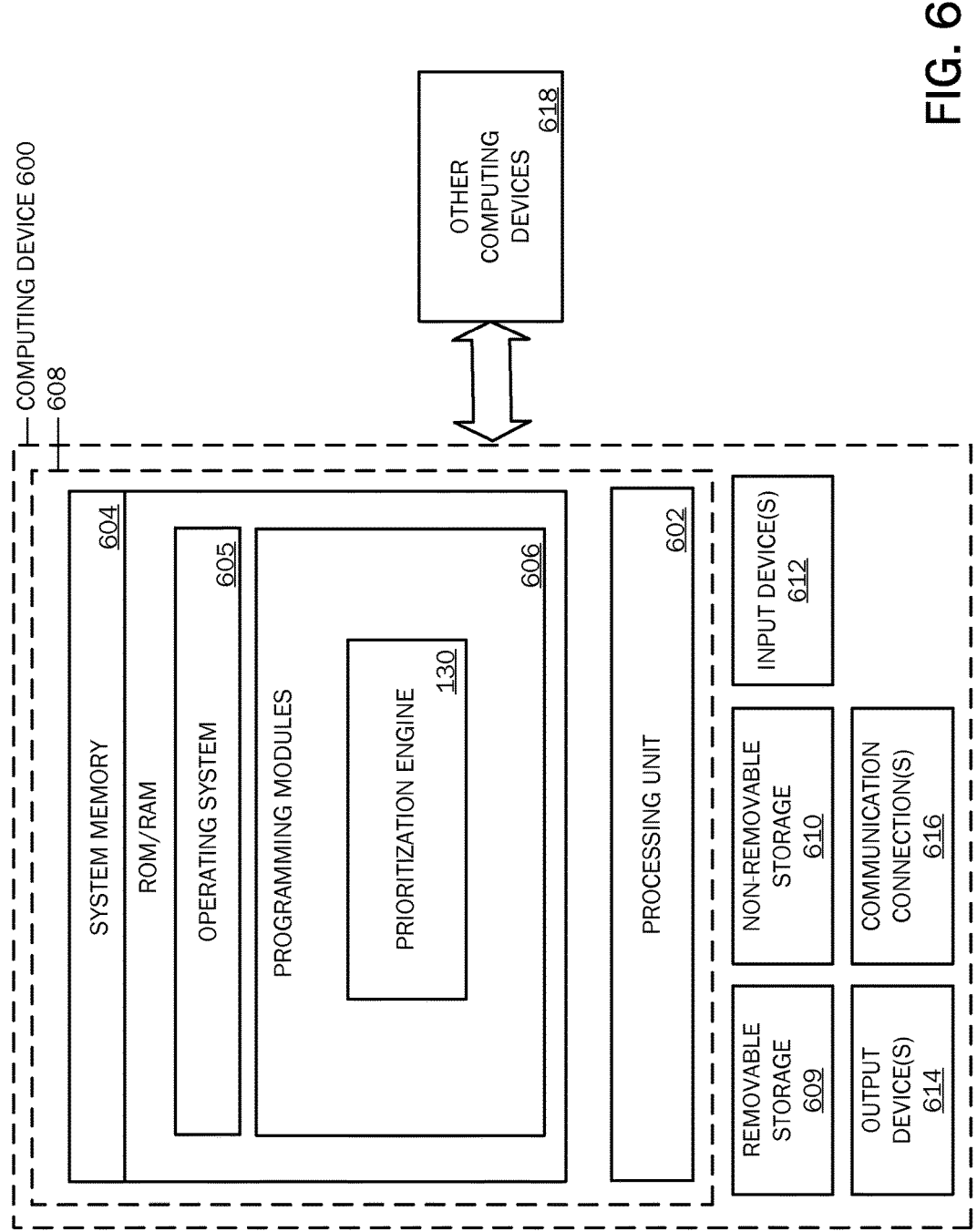
FIG. 6 is a simplified block diagram of a computing device with which embodiments of the present invention may be practiced.

With reference to FIG. 6, a system consistent with embodiments of the invention may include one or more computing devices, such as computing device 600. The computing device 600 may include at least one processing unit 602 and a system memory 604. The system memory 604 may comprise, but is not limited to, volatile (e.g. random access memory (RAM)), non-volatile (e.g. read-only memory (ROM)), flash memory, or any combination. System memory 604 may include operating system 605, one or more programming modules 606, and may include a prioritization engine 130, wherein the prioritization engine 130 is a software application having sufficient computer-executable instructions, which when executed, performs functionalities as described herein. Operating system 605, for example, may be suitable for controlling computing device 600's operation. Furthermore, embodiments of the invention may be practiced in conjunction with a graphics library, other operating systems, or any other application program and is not limited to any particular application or system. This basic configuration is illustrated in FIG. 6 by those components within a dashed line 608. Computing device 600 may also include one or more input device(s) 612 (keyboard, mouse, pen, touch input device, etc.) and one or more output device(s) 614 (e.g., display, speakers, a printer, etc.).

Although embodiments of the present invention have been described as being associated with data stored in memory and other storage mediums, data can also be stored on or read from other types of computer-readable media, such as secondary storage devices, like hard disks, floppy disks, or a CD-ROM, a carrier wave from the Internet, or other forms of RAM or ROM. Further, the disclosed methods' stages may be modified in any manner, including by reordering stages and/or inserting or deleting stages, without departing from the invention.

The computing device 600 may also include additional data storage devices (removable and/or non-removable) such as, for example, magnetic disks, optical disks, or tape. Such additional storage is illustrated in FIG. 6 by a removable storage 609 and a non-removable storage 610. Computing device 600 may also contain a communication connection 616 that may allow device 600 to communicate with other computing devices 618, such as over a network in a distributed computing environment, for example, an intranet or the Internet. Communication connection 616 is one example of communication media.

Program modules, such as the prioritization engine 130, may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable user electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the invention, for example, may be implemented as a computer process (method), a computing system, or as an article of manufacture, such as a computer program product or computer readable media. The computer program product may be a computer storage media readable by a computer system and encoding a computer program of instructions for executing a computer process. Accordingly, the present invention may be embodied in hardware and/or in software (including firmware, resident software, microcode, etc.). In other words, embodiments of the present invention may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

Embodiments of the present invention, for example, are described above with reference to block diagrams and/or operational illustrations of methods, systems, and computer program products according to embodiments of the invention. For example, FIGS. 1-6 and the described functions taking place with respect to each illustration may be considered steps in a process routine performed by one or more local or distributed computing systems. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While the specification includes examples, the invention's scope is indicated by the following claims. Furthermore, while the specification has been described in language specific to structural features and/or methodological acts, the claims are not limited to the features or acts described above. Rather, the specific features and acts described above are disclosed as example for embodiments of the invention.

It will be apparent to those skilled in the art that various modifications or variations may be made in the present invention without departing from the scope or spirit of the invention. Other embodiments of the invention will be apparent to those skilled in the art from consideration of the specification and practice of the invention disclosed herein.

All rights including copyrights in the code included herein are vested in and the property of the Applicant. The Applicant retains and reserves all rights in the code included herein, and grants permission to reproduce the material only in connection with reproduction of the granted patent and for no other purpose.

We claim:

1. A machine-implemented method using one or more computer hardware components to generate a user interface (UI) that includes a plurality of selectable controls comprising:

using the one or more computer hardware components to generate a queue of patient accounts that includes a data structure of prioritized patient accounts in the queue of patient accounts;

using the one or more computer hardware components as part of evaluating patient data of each patient account of the queue of patient accounts and third party data from at least one third party data system to identify issues to be resolved with each patient account;

using the one or more computer hardware components as part of flagging each patient account with alerts to identify additional steps needed to be completed for performing one or more processes of a patient access workflow for each issue identified;

using the one or more computer hardware components to generate a set of weighted factors to apply when calculating priority scores to automatically prioritize patient accounts in the queue of patient accounts to display in the UI including:

generating a first weighted factor for each patient account in the queue of patient accounts according to an amount of time until a healthcare encounter with a healthcare service provider;

generating a second weighted factor for each patient account in the queue of patient accounts according to an estimate of an amount of time to resolve each issue associated with the alerts for each patient account based in part on an estimate of an amount of time to process each of the one or more processes of the patient access workflow for each type of alert;

generating a third weighted factor for each patient account in the queue of patient accounts according to a cost of a service or procedure associated with each patient account;

generating a fourth weighted factor for each patient account in the queue of patient accounts according to a type of insurance network or plan associated with each patient account;

generating a fifth weighted factor for each patient account in the queue of patient accounts according to services or procedures scheduled for each patient account; and generating a sixth weighted factor for each patient account in the queue of patient accounts according to identified discrepancies in each patient account;

using the one or more computer hardware components to calculate a priority score for each patient account of the queue of patient account according to the set of weighted factors that includes: the first weighted factor, the second weighted factor, the third weighted factor, the fourth weighted factor, the fifth weighted factor, and the sixth weighted factor;

using the one or more computer hardware components to display a patient account having a highest priority score in the UI before displaying other patient accounts in the queue of patient accounts;

using the one or more computer hardware components to display the plurality of selectable controls with the UI including an alerts UI control, a demographics UI control, a coverage UI control, a medical necessity UI control, a pre-certification UI control, an estimate UI control, and a next UI control, wherein:

in response to selection of the alerts UI control, display an overview page in the UI for the patient account with the highest priority score from the queue according to the set of weighted factors, the overview page including:

one or more of a general alert display portion, a demographics alert display portion, a coverage alert display portion, a medical necessity alert display portion, a pre-certification alert display portion, and a claims alert display portion, and one or more selectable alert UI elements displayed in one or more of the general alert display portion, the demographics alert display portion, the coverage alert display portion, the medical necessity alert display portion, the pre-certification alert display portion, and the claims alert display portion for the patient account with the highest priority score, and in response to selection of a selectable alert UI element, display a UI page for a corresponding patient access workflow process associated with one or more demographics alerts, coverage alerts, medical necessity alerts, pre-certification alerts, and claims alerts;

in response to actuation of the next UI control that operates to display a next patient account in the UI having a next highest priority score according to the set of weighted factors, using the one or more computer hardware components to display the next patient account in the UI having the next highest priority score.

2. The method of claim 1, further comprising-receiving results from one or more automated patient access workflow processes including one or more of:
demographics information verification;
coverage information verification;
medical necessity validation;
pre-certification;
estimation;
financial clearance; or
collections.

3. The method of claim 1, further comprising using the one or more computer hardware components to generate general alerts, demographics alerts, coverage alerts, medical necessity alerts, pre-certification alerts, and claims alerts in the UI, wherein the UI includes the selectable controls that operate to switch between pages that include the general alerts, demographics alerts, coverage alerts, medical necessity alerts, pre-certification alerts, and claims alerts in the UI for the patient account.

4. The method of claim 1, further comprising determining types of the alerts to be resolved to clear each patient account.

5. The method of claim 1, further comprising receiving a request for a next patient account and providing the next patient account with the next highest priority score for display in the UI.

6. The method of claim 1, wherein evaluating patient data and flagging each patient account occurs during one or more automated patient access workflow processes.

7. The method of claim 1, further comprising generating additional weighted factors to calculate the priority score for each patient account including:
a seventh weighted factor corresponding to whether each patient account is self-pay or has insurance coverage; and
an eighth weighted factor corresponding to which payer is providing insurance coverage for each patient account.

8. The method of claim 7, further comprising generating additional weighted factors including:

a ninth weighted factor corresponding to historical claim denials by the payer providing insurance coverage for the services or procedures scheduled for the healthcare encounter; and a tenth weighted factor corresponding to statistical information linking a likelihood of non-payment associated with each patient account.

9. The method of claim 1, further comprising displaying the selectable alert UI elements in groups within the overview based on automated patient access workflow processes.

10. A system to generate a user interface (UI) that includes a plurality of selectable controls comprising:
   one or more computer hardware components that include a processor, memory, a computer display, the UI, and a communication network;
   one or more of automated patient workflow engines operable with the one or more computer hardware components in communication over the communication network with at least one third party data system and operable to evaluate patient data of each patient account against data stored by the at least one third party data system to identify issues to be resolved with each patient account and display alerts to identify additional steps needed to be completed for performing one or more processes of a patient access workflow to clear each patient account;
   a prioritization engine operable with the one or more computer hardware components to:
      generate a queue of patient accounts that includes a data structure of prioritized patient accounts in the queue of patient accounts;
      generate a set of weighted factors to apply when calculating priority scores to automatically prioritize patient accounts in the queue of patient accounts according to the set of weighted factors such that a patient account having a highest priority score is displayed in the UI before other patient accounts in the queue of patient accounts, the prioritization engine to:
         generate a first weighted factor for each patient account in the queue of patient accounts according to an amount of time until a healthcare encounter with a healthcare service provider;
         generate a second weighted factor for each patient account in the queue of patient accounts according to an estimate of an amount of time to resolve each issue associated with the alerts for each patient account based in part on an estimate of an amount of time to process each of the one or more processes of the patient access workflow for each type of alert;
         generate a third weighted factor for each patient account in the queue of patient accounts according to a cost of a service or procedure associated with each patient account;
         generate a fourth weighted factor for each patient account in the queue of patient accounts according to a type of insurance network or plan associated with each patient account;
         generate a fifth weighted factor for each patient account in the queue of patient accounts according to services or procedures scheduled for each patient account; and
         generate a sixth weighted factor for each patient account in the queue of patient accounts according to identified discrepancies in each patient account;
      calculate a priority score for each patient account of the queue of patient accounts according to the set of weighted factors-that includes: the first weighted factor, the second weighted factor, the third weighted factor, the fourth weighted factor, the fifth weighted factor, and the sixth weighted factor; and
      order each patient account within the queue of patient accounts based on a corresponding priority score; and
   the UI operable with the one or more computer hardware components to display
   the plurality of selectable controls including an alerts UI control, a demographics UI control, a coverage UI control, a medical necessity UI control, a pre-certification UI control, an estimate UI control, and a next UI control, wherein:
      in response to selection of the alerts UI control, display an overview page in the UI for the patient account with the highest priority score from the queue according to the set of weighted factors, the overview page including:
         one or more of a general alert display portion, a demographics alert display portion, a coverage alert display portion, a medical necessity alert display portion, a pre-certification alert display portion, and a claims alert display portion, and
         one or more selectable alert UI elements displayed in one or more of the general alert display portion, the demographics alert display portion, the coverage alert display portion, the medical necessity alert display portion, the pre-certification alert display portion, and the claims alert display portion for the patient account with the highest priority score, and
      in response to selection of a selectable alert UI element, display a UI page for a corresponding patient access workflow process associated with one or more demographics alerts, coverage alerts, medical necessity alerts, pre-certification alerts, and claims alerts; and
      in response to actuation of the next UI control that operates to display a next patient account in the UI having a next highest priority score according to the set of weighted factors, the UI displays the next patient account having the next highest priority score.

11. The system of claim 10, wherein the one or more automated patient workflow engines use one or more of:
   alerts data;
   demographics information verification data;
   coverage information verification data;
   medical necessity validation data;
   pre-certification data;
   estimate data;
   financial clearance data; or
   collections data.

12. The system of claim 10, wherein the weighted factors are based on historical data.

13. The system of claim 10, further to calculate the priority score for each patient account according to:
   a seventh weighted factor corresponding to whether each patient account is self-pay or has insurance coverage; and
   an eighth weighted factor corresponding to a specific payer providing insurance for each patient account.

14. The system of claim 10, further operable to receive a request for a next patient account and provide the next patient account with a next highest priority score.

15. The system of claim 10, wherein selection of a selectable alert UI element operates to display at least one of:
   a page from the one or more automated patient workflow engine that set the associated alert containing the corresponding patient data and allow the issue to be addressed; and
   additional information about the issue associated with the associated alert.

16. A non-transitory computer readable medium containing executable instructions which, when executed, generate a user interface (UI) that includes a plurality of selectable controls and:
   use one or more computer hardware components to generate a queue of patient accounts that includes a data structure of prioritized patient accounts in the queue of patient accounts;
   use one or more computer hardware components to evaluate patient data of each patient account of the queue of patient accounts and third party data from at least one third party data system to identify issues to be resolved with each patient account;
   use the one or more computer hardware components to flag each patient account with alerts to identify additional steps needed to be completed for performing one or more processes of a patient access workflow for each issue identified;
   use the one or more computer hardware components to generate a set of weighted factors to apply when calculating priority scores to automatically prioritize patient accounts in the queue of patient accounts to display in the UI including:
      generating a first weighted factor for each patient account in the queue of patient accounts according to an amount of time until a healthcare encounter with a healthcare service provider;
      generating a second weighted factor for each patient account in the queue of patient accounts according to an estimate of an amount of time to resolve each issue associated with the alerts for each patient account based in part on an estimate of an amount of time to process each of the one or more processes of the patient access workflow for each type of alert;
      generating a third weighted factor for each patient account in the queue of patient accounts according to a cost of a service or procedure associated with each patient account;
      generating a fourth weighted factor for each patient account in the queue of patient accounts according to a type of insurance network or plan associated with each patient account;
      generating a fifth weighted factor for each patient account in the queue of patient accounts according to services or procedures scheduled for each patient account; and
      generating a sixth weighted factor for each patient account in the queue of patient accounts according to identified discrepancies in each patient account;
   use the one or more computer hardware components to calculate a priority score for each patient account according to the set of weighted factors that includes: the first weighted factor, the second weighted factor, the third weighted factor, the fourth weighted factor, the fifth weighted factor, and the sixth weighted factor;
   use the one or more computer hardware components to order each patient account within the queue of patient accounts based on the priority score;
   use the one or more computer hardware components to display a patient account having a highest priority score in the UI before displaying other patient accounts in the queue of patient accounts;
   use the one or more computer hardware components to display selectable controls with the UI including an alerts UI control, a demographics UI control, a coverage UI control, a medical necessity UI control, a pre-certification UI control, an estimate UI control, and a next UI control, wherein:
      in response to selection of the alerts UI control, display an overview page in the UI for the patient account with the highest priority score from the queue according to the set of weighted factors, the overview page including:
         one or more of a general alert display portion, a demographics alert display portion, a coverage alert display portion, a medical necessity alert display portion, a pre-certification alert display portion, and a claims alert display portion, and
         one or more selectable alert UI elements displayed in one or more of the general alert display portion, the demographics alert display portion, the coverage alert display portion, the medical necessity alert display portion, the pre-certification alert display portion, and the claims alert display portion for the patient account with the highest priority score, and
      in response to selection of a selectable alert UI element, display a UI page for a corresponding patient access workflow process associated with one or more demographics alerts, coverage alerts, medical necessity alerts, pre-certification alerts, and claims alerts; and
      in response to actuation of the next UI control that operates to display a next patient account in the UI having a next highest priority score according to the set of weighted factors, use the one or more computer hardware components to display the next patient account in the UI having the next highest priority score.

17. The non-transitory computer readable medium of claim 16, wherein determining a priority score for each patient account further comprises generating:
   a seventh weighted factor corresponding to whether the patient account is self-pay or has insurance coverage; and
   an eighth weighted factor corresponding to a specific payer providing insurance for the patient account.

* * * * *